United States Patent
Urbanowicz et al.

(10) Patent No.: US 8,158,523 B2
(45) Date of Patent: Apr. 17, 2012

(54) QUANTIFICATION OF HYDROPHOBIC AND HYDROPHILIC PROPERTIES OF MATERIALS

(75) Inventors: Adam Michal Urbanowicz, Wroclaw (PL); Mikhaïl Baklanov, Veltem-Beisem (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 787 days.

(21) Appl. No.: 12/204,165

(22) Filed: Sep. 4, 2008

(65) Prior Publication Data
US 2009/0068768 A1 Mar. 12, 2009

Related U.S. Application Data

(60) Provisional application No. 60/970,844, filed on Sep. 7, 2007.

(30) Foreign Application Priority Data

Dec. 10, 2007 (EP) .................................... 07076062

(51) Int. Cl.
*H01L 21/302* (2006.01)
(52) U.S. Cl. .......... 438/706; 438/700; 438/704; 216/37; 216/67
(58) Field of Classification Search .......... 438/700–708; 216/37, 67
See application file for complete search history.

(56) References Cited

U.S. PATENT DOCUMENTS
5,221,426 A 6/1993 Tessier et al.

OTHER PUBLICATIONS

Edward Sosnin et al. Journal of Photochemistry and Photobiology C: Photochemistry Reviews, vol. 7, (2006), pp. 145-163.*
Toshiaki Yamamoto et al. Plasma Chemistry and Plasma Processing, vol. 24, No. 1, Mar. 2004 pp. 1-12.*
N.Krstulovic et al. Journal of Physics, D (Appl.Phys.) vol. 39, (2006), pp. 3799-3804.*
Kuo et al., "Room-temperature copper etching based on a plasma-copper reaction." Applied Physics Letters, 2001, vol. 78, No. 7 (2001).
Macko et al., Plasma Sources Sci. Technol., 13 (2004), p. 251-262.
Urbanowicz et al., "Effect of Helium Plasma on Low-k damage during Dry Resist Strip" Proceedings of plasma etch and strip workshop, Leuven, 2007.

* cited by examiner

*Primary Examiner* — Nadine G Norton
*Assistant Examiner* — Maki Angadi
(74) *Attorney, Agent, or Firm* — Knobbe Martens Olson & Bear LLP

(57) ABSTRACT

A non-destructive and simple analytical method is provided which allows in situ monitoring of plasma damage during the plasma processing such as resist stripping. If a low-k film is damaged during plasma processing, one of the reaction products is water, which is remained adsorbed onto the low-k film (into pores), if the temperature is lower than 100-150 C. A plasma (e.g. He) that emits high energy EUV photons (E>20 eV) which is able to destruct water molecules forming electronically excited oxygen atoms is used to detect the adsorbed water. The excited oxygen is detected from optical emission at 777 nm. Therefore, the higher the adsorbed water concentration (higher damage), a more intensive (oxygen) signal is detected. Therefore, intensity of oxygen signal is a measure of plasma damage in the previous strip step. The proposed analytical method can be performed in-situ immediately after plasma processing and most preferred the optical emission of oxygen radicals is monitored during the de-chucking step in the plasma chamber.

23 Claims, 9 Drawing Sheets

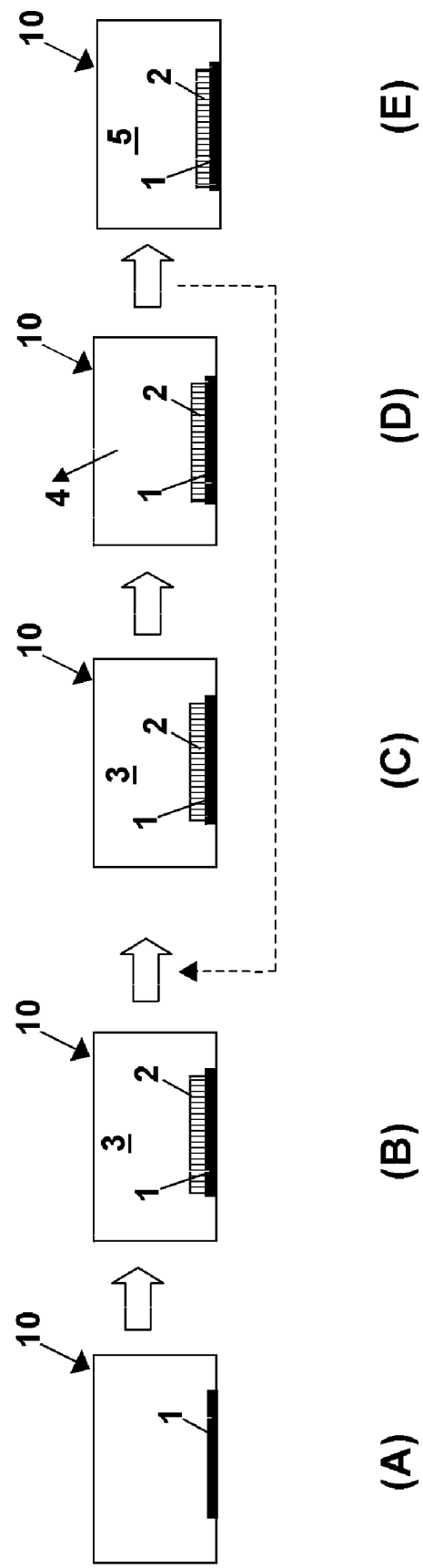
FIG. 1 – PRIOR ART

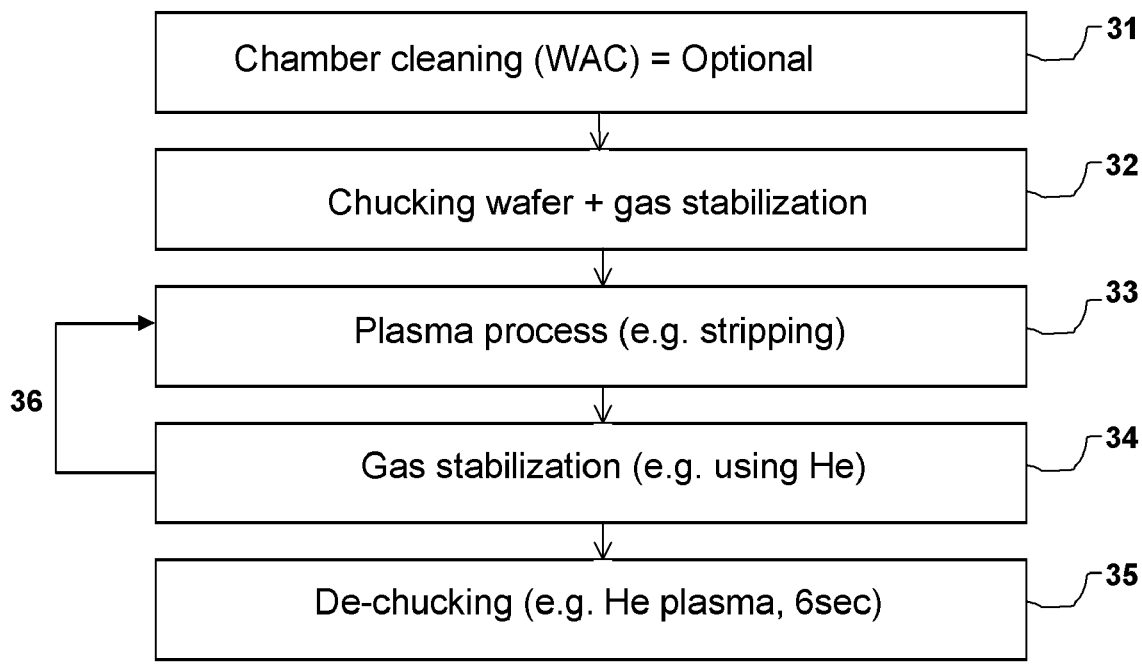
FIG. 2 – PRIOR ART
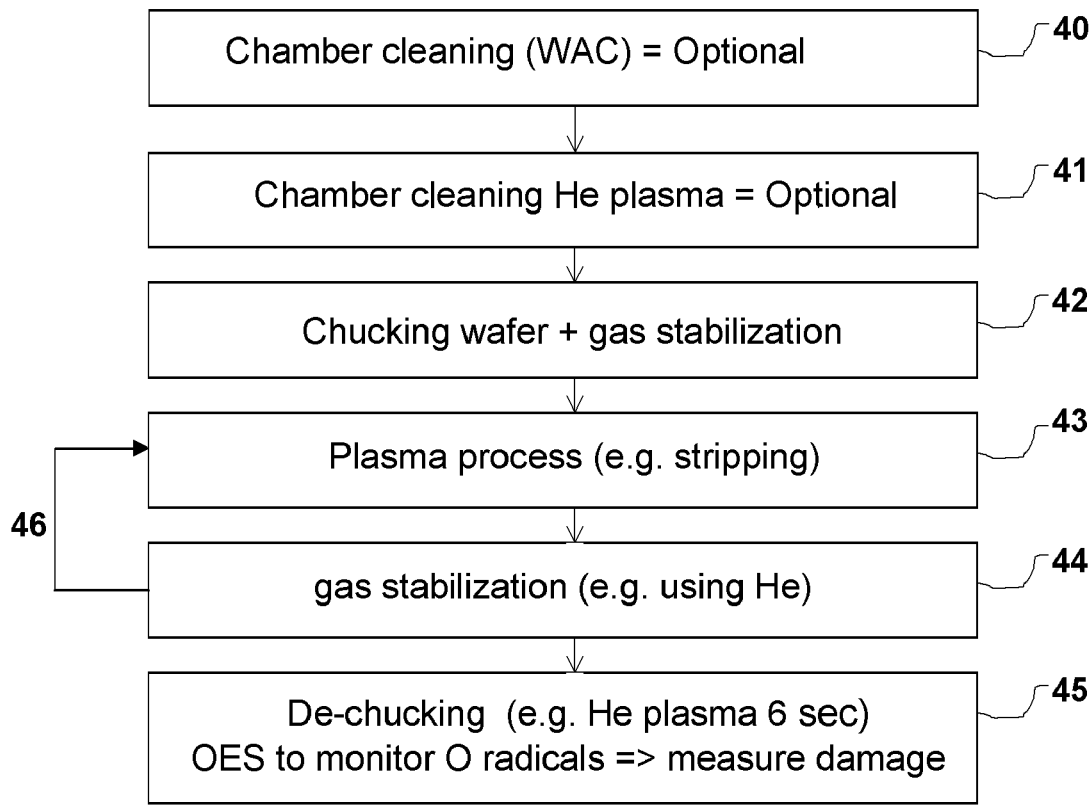
FIG. 4

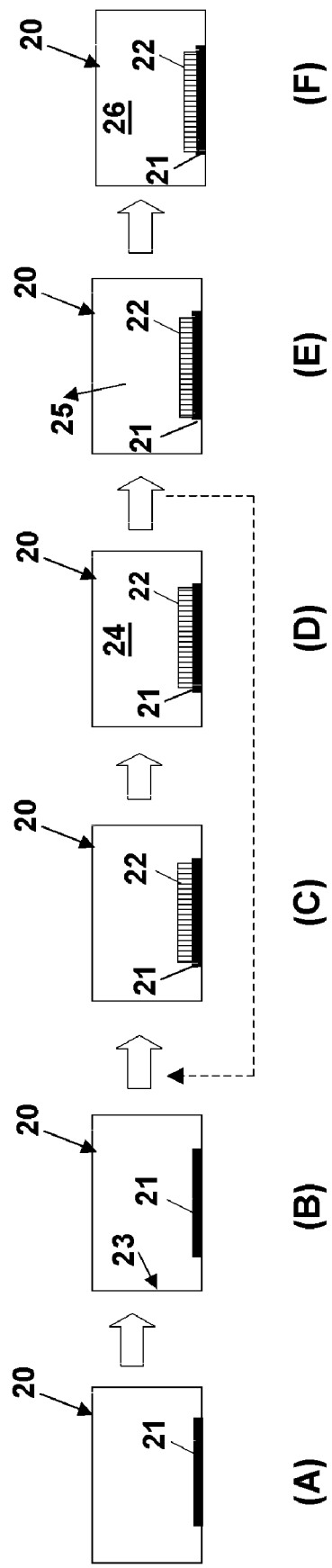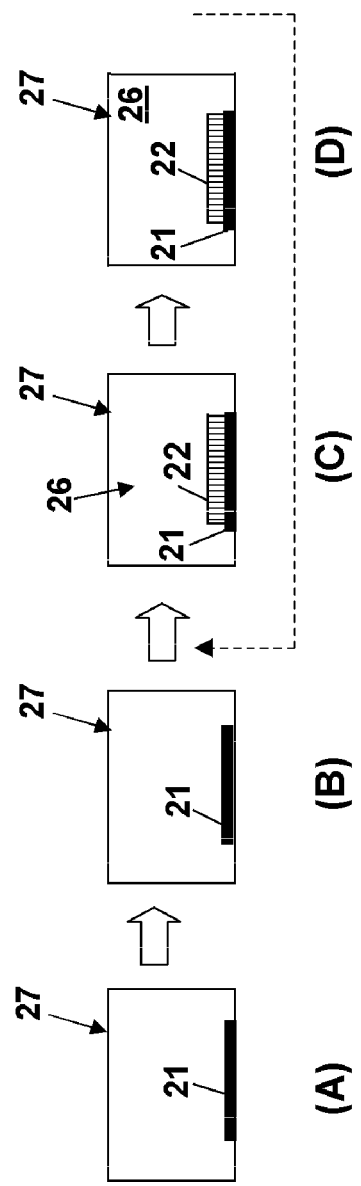
FIG. 3
FIG. 6

QUANTIFICATION OF HYDROPHOBIC AND HYDROPHILIC PROPERTIES OF MATERIALS

CROSS-REFERENCE TO RELATED APPLICATIONS

This application claims the benefit under 35 U.S.C. §119 (e) of U.S. provisional application Ser. No. 60/970,844, filed Sep. 7, 2007, and claims the benefit under 35 U.S.C. §119(a)-(d) of European application No. 07076062.4, filed Dec. 10, 2007, the disclosures of which are hereby expressly incorporated by reference in their entirety and are hereby expressly made a portion of this application.

FIELD OF THE INVENTION

The preferred embodiments relate to hydrophobic and hydrophilic properties of materials. More particularly, the preferred embodiments relate to a method for quantifying hydrophobic and/or hydrophilic properties of a material, e.g. a porous material. The method according to preferred embodiments can be used for in situ evaluation of plasma damage of materials caused by a plasma treatment.

BACKGROUND OF THE INVENTION

A critical issue in integration of porous materials, such as e.g. low-k materials, in semiconductor processing is the degradation of their properties, e.g. their dielectric properties, during plasma etching and/or resist stripping. Porous low-k materials are more sensitive to chemical and plasma damage in comparison to conventional dielectric materials such as, for example, silicon dioxide. The open porosity of porous low-k materials significantly increases diffusivity of plasma species, e.g. plasma radicals, or water from air. Because of this, porous dielectrics are very sensitive to plasma induced damage during processing steps such as e.g. etching and stripping. A damage mechanism which may occur is the replacement of hydrophobic methyl groups by hydrophilic OH groups. As a result, polar water groups are incorporated into the porous structure which may increase the dielectric constant or k-value of the material. For example, in carbon doped silica (SiOC) a Si—$CH_3$ bond may be broken and carbon may be replaced by a silicon-dangling bond, which leads to carbon depletion. This carbon depletion results in the formation of silanol (Si—OH) through a variety of intermediate reactions. This leads to an increase in k-value for the damaged portion of the porous material and converts the inherently hydrophobic low-k material into a hydrophilic material. Subsequent adsorption of moisture, e.g. water, or other polar molecules having high polarizability, mediated by hydrogen bonding, can significantly increase the effective k-value of the material, e.g. to a k-value>>80.

FIG. 1 schematically illustrates a plasma process sequence used in semiconductor device processing to perform a resist stripping or etching on a porous low-k dielectric material as used in the prior art. FIG. 2 shows a flow chart illustrating main processing steps according the prior art plasma process as illustrated in FIG. 1. A first step (step (A) in FIG. 1 and step 31 in FIG. 2), which may be optional, is a chamber cleaning step which uses a cleaning plasma such as e.g. an $O_2/SF_6$ or on $O_2Cl_2$ plasma. This step may also be referred to as Waferless Auto Cleaning (WAC). The plasma chamber 10 has a wafer holder 1, also referred to as chuck. In a next step (step (B) in FIG. 1 and step 32 in FIG. 2), a wafer 2 comprising a low-k dielectric material to be processed is introduced into the plasma chamber 10 and fixed to the chuck 1 by performing a chucking step. The chucking step can be an electrostatic (plasma-free) chucking process or a plasma step performed by applying e.g. a He plasma (e.g. 400 W, 12 eV, 6 seconds). After fixing the wafer 2 to the chuck 1 the plasma chamber 10 is filled with gas species 3 needed to perform a required plasma process, also referred to as gas stabilization step. The next step (step (C) in FIG. 1 and step 33 in FIG. 2) is a plasma process step which can e.g. be a reactive ion etching of the low-k dielectric material or a resist stripping step using, for example an O-rich plasma. After finalizing the plasma process step, another gas stabilization step (step (D) in FIG. 1 and step 34 in FIG. 2) is introduced to remove reactant gasses (indicated by arrow 4). Steps (C) and (D) can, if desired, be repeated in order to perform more than one plasma process in the plasma chamber 10 (step 36 in FIG. 2). In a last step (step (E) in FIG. 1 and step 35 in FIG. 2) the wafer 2 is released from the chuck 1 using a de-chucking step e.g. by applying a He plasma 5 (e.g. 400 W, 12 eV, 6 seconds).

In general, plasma damage is evaluated after having performed a plasma processing step using complicated analytical techniques like, for example, Fourier Transform Infra Red (FTIR), Time of Flight Secondary Ion Mass Spectrometry (TOF-SIMS), X-Ray Photoelectron Spectroscopy (XPS). These methods are very time consuming and most of them are destructive and not suitable for being used with patterned wafers comprising dense structures (to analyse damage on sidewalls of dense structures). Therefore, it is an important issue to develop a simple and non-destructive method which allows evaluation of plasma damage immediately after plasma processing such that the process can be tuned further to avoid plasma damage and/or damaged samples can be eliminated from the process flow.

Thus, the prior art proposes several methods to determine low-k damage but they have drawbacks and shortcomings. There is no method available in the prior art that allows a quick and non-destructive evaluation of plasma damage immediately after performing plasma processing. There is a need for such a method and a need for having a simple non-destructive method not only in further exploring and screening different low-k materials but also in future fabrication flows of microchips of future technologies.

SUMMARY OF THE INVENTION

A good method for quantifying hydrophilic and/or hydrophobic properties of a material is provided. The method can be performed quickly, is easily applicable and is non-destructive. The method can be used for determination, evaluation and/or quantification of plasma damage caused to materials, e.g. porous material, by plasma processes such as plasma etching or stripping, e.g. reactive ion etching and/or resist stripping.

In its broadest form, the preferred embodiments provide a method for quantifying hydrophilic and/or hydrophobic properties of a material. The method comprises:
  exposing the material to a noble gas plasma, the noble gas plasma being able to emit photons having sufficient energy to cause photolysis of molecules adsorbed to the material so as to release radicals of these adsorbed molecules,
  detecting the amount of released radicals, and
  from the amount of released radicals quantifying the hydrophilic and/or hydrophobic properties of the material.

In one embodiment, a method is provided for quantifying hydrophilic and/or hydrophobic properties of a material. The method comprises:

exposing the material to a noble gas plasma, the noble gas plasma being able to emit Extreme Ultra Violet and/or Vacuum Ultra Violet photons having sufficient energy to cause photolysis of water molecules adsorbed to the material so as to release oxygen, hydrogen and/or hydroxyl radicals, detecting the amount of released oxygen, hydrogen and/or hydroxyl radicals, and from the amount of released oxygen, hydrogen and/or hydroxyl radicals quantifying the hydrophilic and/or hydrophobic properties of the material.

An advantage of the method according to preferred embodiments is that it is not destructive and can be performed in-situ as well as ex-situ.

Detecting the amount of released oxygen, hydrogen and/or hydroxyl radicals may be performed by optical emission spectroscopy, laser induced fluorescence or mass spectrometry.

According to preferred embodiments, detecting the amount of released oxygen, hydrogen and/or hydroxyl radicals may be performed by detecting oxygen radicals using optical emission spectroscopy at a predetermined wavelength, e.g. 777 nm.

According to preferred embodiments, the method may furthermore comprise, from the quantification of the hydrophilic or hydrophobic properties of the material, determining a degree of damage of the material resulting from plasma processes performed on the material.

The method according to preferred embodiments may be performed in a reactive ion etching chamber using a He or Ar plasma.

According to preferred embodiments, the method may be performed "in-situ", i.e. it may be performed during or immediately after performing processes on the material, e.g. during or immediately after performing plasma processes to a porous material, e.g. porous low-k material, and may be performed in a same plasma chamber as the processes.

According to other preferred embodiments, the method may be performed "ex-situ", i.e. it may be performed as an individual analytical measurement.

According to preferred embodiments, the material may be a porous material, such as for example a low-k dielectric material having pores.

The preferred embodiments also provide the use of the method according to preferred embodiments for quantifying plasma damage of a material, e.g. porous material, after etching of that material.

Particular and preferred aspects of the preferred embodiments are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 1 schematically illustrates a processing sequence to perform a plasma process according to the prior art.

FIG. 2 shows a flow chart illustrating main processing steps of the prior art plasma process as illustrated in FIG. 1.

FIG. 3 schematically illustrates a method according to a preferred embodiment for in-situ monitoring of plasma damage.

FIG. 4 shows a flow chart illustrating main processing steps of the method schematically illustrated in FIG. 3.

FIG. 6 schematically illustrates a method according to a preferred embodiment for ex-situ monitoring of plasma damage.

DETAILED DESCRIPTION OF PREFERRED EMBODIMENT

Figure 5:
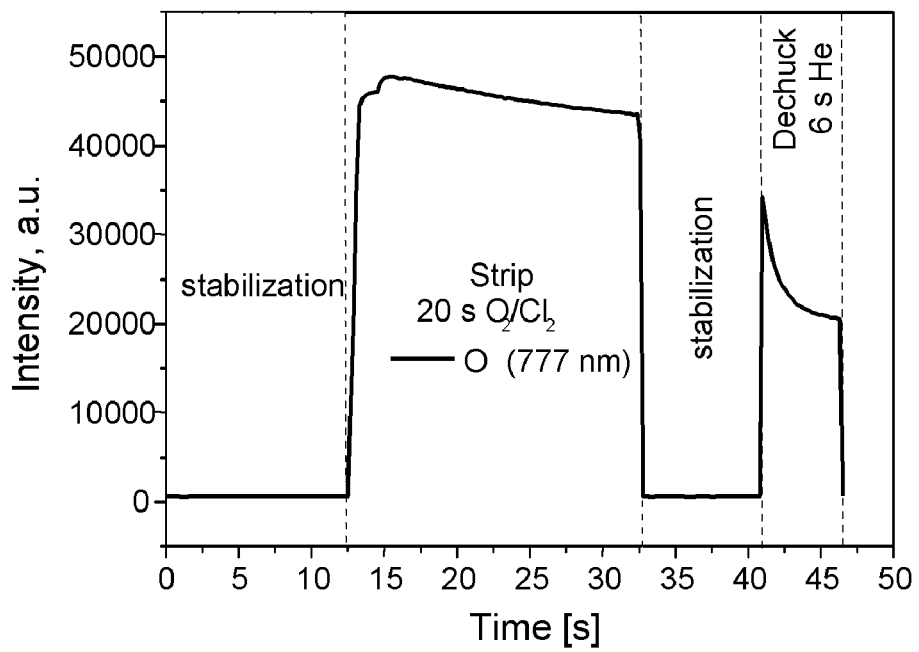
FIG. 5 shows an optical emission spectrum for a signal at wavelength 777 nm which corresponds to a 5P→5S transition of electronically excited oxygen radicals.

Preferred embodiments will be described below with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of preferred embodiments, various features of the invention are sometimes grouped together in a single embodiment, figures or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing provided embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that preferred embodiments may be practised without these specific details. In other instances, well-known methods, structures and techniques have not been shown in detail in order not to obscure an understanding of this description.

The following terms are provided solely to aid in the understanding of the preferred embodiments.

The terms "electrostatic chucking" and "electrostatic de-chucking" refer to steps which are used to respectively fix and release a sample, e.g. a wafer, onto or from a wafer holder in a plasma etch chamber. To perform "chucking" or "de-chucking" the wafer can shortly be exposed to a plasma, e.g. a He plasma, to charge or discharge the sample, e.g. wafer, and in that way fix or release the sample, e.g. wafer, onto from the sample holder.

A detailed description of several preferred embodiments is provided. It is clear that other preferred embodiments can be configured according to the knowledge of persons skilled in the art without departing from the technical teaching of the invention, the invention being limited only by the terms of the appended claims.

According to preferred embodiments a method is provided for quantifying hydrophilic and/or hydrophobic properties of materials, for example porous materials such as e.g. low-k materials.

The method comprises:
exposing the material to a noble gas plasma, the noble gas plasma being able to emit Extreme Ultra Violet and/or Vacuum Ultra Violet photons having sufficient energy to cause photolysis of water molecules adsorbed to the material so as to release oxygen, hydrogen and/or hydroxyl radicals,
detecting the amount of released oxygen, hydrogen and/or hydroxyl radicals, and
from the amount of released oxygen, hydrogen and/or hydroxyl radicals quantifying the hydrophilic and/or hydrophobic properties of the material.

The method according to preferred embodiments is quick, easily applicable and non-destructive.

The method according to preferred embodiments can be used for the quantification of plasma damage in porous materials, e.g. low-k materials, caused during particular steps during processing, e.g. etching and/or stripping steps. During particular steps, such as etching and/or stripping steps, in the manufacturing process of semiconductor devices comprising porous materials, for example porous low-k materials, these materials may get damaged. For example, the porous materials used may loose organic hydrophobic groups during plasma etch and/or stripping processes. As a result, they become hydrophilic which makes them able to adsorb moisture and other polar molecules that may increase the dielectric constant or k-value of the materials, thereby decreasing their dielectric properties. The degree of plasma damage introduced in the porous material, e.g. low-k material, during these processes, e.g. plasma etch and/or strip processes may be evaluated by using known techniques such as e.g. Fourier Transform Infra Red (FTIR) or Water based Ellipsometry (EP). However, as already discussed these techniques are complicated, time consuming and/or destructive and are not applicable to analyse patterned dense structures. Hence, according to these embodiments, the hydrophilic and/or hydrophobic properties of the porous material are a measure for the degree of damage of the porous material. According to preferred embodiments, the porous material may be a low-k material or may be an ultra low-k material.

According to preferred embodiments, adsorption of water, also referred to as adsorption of hydrophilic groups, can occur as a result or by-product of the reaction of organic hydrophobic groups during exposure of a material, e.g. porous material, to an oxidizing plasma e.g. an $O_2$ plasma. In case the material is a porous low-k material, relatively low processing temperatures of between 20° C. and 200° C., e.g. a process temperature of 30° C., during e.g. a stripping process may be sufficient for $CO_2$ desorption but a significant part of water molecules still remains inside the film in a chemisorbed state.

The method according to preferred embodiments is based on the exposure of a material to a plasma that is able to emit EUV (Extreme Ultra Violet) and/or VUV (far or Vacuum Ultra Violet) photons having sufficient energy to dissociate water molecules adsorbed to the material so as to release oxygen, hydrogen and/or hydroxyl radicals. The plasma may, for example, be a low pressure plasma with a minimum power of approximately 100 Watt (no bias is applied). According to preferred embodiments the plasma may comprise at least one compound selected from the group of noble gases with an atomic weight less than Xe, such as He and Ar. More heavy noble gases will emit radiation with an energy that is not sufficient to dissociate water. In preferred embodiments, noble gases are used because they do not chemically react with the material of interest, e.g. with a low-k material. It was found that exposure to a noble gas plasma causes photolysis of water incorporated in or adsorbed to the surface or into pores of the material, thereby forming O*, OH* and/or H* radicals.

A method according to preferred embodiments may make use of chemiluminescence. Chemiluminescence or, in other words, emission of light, is the result of a decay from an excited state of a molecule or atom to a lower energy level. In theory one photon of light should be emitted for each molecule or atom going back to a lower energy level. Chemiluminescence can be monitored using optical emission spectrometry (OES).

According to preferred embodiments, chemiluminescence of the O*, OH* and/or H* radicals can be used to determine the hydrophilic and/or hydrophobic properties of the material. Hence, according to preferred embodiments, the appearance of O*, OH* and/or H* radicals can be related to the photolysis of water adsorbed on or into the pores of a material, e.g. in the pores of a porous material such as porous low-k materials, or in openings etched in the material. On the other hand, according to other preferred embodiments, the appearance of O* radicals can be related to the desorption, e.g. photo-induced desorption, of chemisorbed oxygen atoms or molecules trapped on or into the pores of a material or in openings etched in the material as a result of the exposure of the material to a plasma that is suitable to emit EUV and/or VUV photons.

Products of the above-described reactions, i.e. O*, OH* and/or H* radicals can be detected by, for example, Optical Emission Spectrometry (OES). Analysis of radiation intensities at particular wavelengths may then reveal quantitative information about the hydrophilic and/or hydrophobic properties of the material under examination. For example, for O* radicals, analysis of radiation intensities at a wavelength of 777 nm may give information about hydrophilic and/or hydrophobic properties of the material. Furthermore, H* radicals can be monitored at a wavelength of 656 nm and OH* radicals can be monitored at a wavelength of 309 nm. OES may be performed or a spectrum may simultaneously be monitored during the exposure of the material to the noble gas plasma causing the photolysis of adsorbed water. In the particular case of the method according to the preferred embodiments being used to determine damage of a low-k dielectric material after plasma processes, the information obtained from the EOS spectrum may then be used to determine the degree of damage induced by the plasma process such as etching processes and/or stripping processes.

According to other preferred embodiments, alternative detection methods may be used to detect the presence of O*, OH* and/or H* radicals. Examples may for example be laser induced fluorescence and mass spectrometry.

Hereinafter, preferred embodiments will mainly be described by means of porous low-k materials onto which plasma processes such as etching and stripping have been performed which resulted in plasma damage of the porous low-k materials. It has, however, to be understood that this is only for the ease of explanation and is not intended to limit the preferred embodiments. The method according to preferred embodiments may also be applied to determine hydrophilic and/or hydrophobic properties of other materials. For example the method according to preferred embodiments can be used to estimate an amount of adsorbed moisture or oxygen on a sidewall of a plasma etch chamber (A. M. Urbanowicz et al., Proceedings of Plasma etch and strip workshop, Leuven, 2007). Furthermore, the preferred embodiments will be described by means of the method being used for determining damage caused to low-k materials by plasma processes such as plasma etching and/or stripping. Again, this is not intended to limit the preferred embodiments in any way.

According to preferred embodiments, the method may, for example be applied to low-k materials, e.g. ultra low-k materials having pore sizes between 2 nm and 10 nm. Ultra low-k materials may be defined as materials having a porosity of higher than 30%.

Porous low-k materials, which may also be referred to as low-k dielectrics, such as e.g. porous carbon doped silica (SiOC), (e.g. commercially available BDIIx®) and which may usually be deposited using Plasma Enhanced Chemical Vapor Deposition (PE-CVD) are very sensitive to chemical and plasma damage. These porous low-k materials may, for example, have an open porosity close to 25% based on total material volume, an average pore radius of 0.8-0.9 nm and an average k-value of 2.5. As already described above, degradation of the dielectric constant of a low-k material may usually be the result from adsorbed water to locations where damage is caused to the material, This water is formed as a by-product of reaction of organic hydrophobic groups (≡Si—CH$_3$ in case of carbon doped silica) during exposure of the material to an oxidizing plasma such as an O$_2$ plasma used during, for example, resist stripping, into the pores of the low-k material. The reaction in case of carbon doped silica can be written down as:

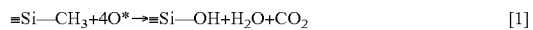

≡Si—CH$_3$+4O*→≡Si—OH+H$_2$O+CO$_2$   [1]

Adsorbed water molecules significantly increase the k-value of the low-k dielectric material because the k-value of water is about 80 at 20° C. As low-k materials may, for example, be used to isolate interconnect structures in a semiconductor devices, it may be important to know or be able to detect different aspects of plasma damage occurred during the different processing steps used to e.g. pattern the low-k dielectric material, e.g. etching and/or stripping processes.

It is known that an oxygen plasma, which is, for example, used for resist stripping, emits radiation with a wavelength of 777 nm which corresponds to 5P→5S transition of electronically excited oxygen radicals (see P. Macko et al., Plasma Sources Sci. Technol., 13 (2004), p. 251-262). However, it was surprisingly found that radiation with a same wavelength is emitted during a de-chucking step used to release a sample, e.g. wafer, from a wafer holder after plasma processing. The peak intensity at 777 nm further depends on preliminary treatment of the material that was plasma treated, e.g. a porous low-k material. In other words, the peak intensity at 777 nm caused by the presence of O* radicals depends on the amount of damage caused to the low-k material when exposed to e.g. an oxygen plasma during process steps such as plasma etching or stripping.

For evaluations of plasma damage due to plasma processing such as resist stripping and dry etching in a reactive ion plasma chamber, the evaluation of the plasma damage can be performed immediately after the plasma process.

According to preferred embodiments the exposure of the material under examination to the noble gas plasma and detection of the formed radicals may be performed "ex-situ" or in other words the material is transferred to a suitable plasma chamber for being exposed there to the noble gas plasma. According to other preferred embodiments, the exposure to the noble gas plasma and detection of the formed radicals may also be performed "in-situ", or in other words immediately after plasma processing, e.g. plasma etching or stripping of the material in the same plasma chamber as where the plasma processing was performed. In other words, the hydrophobic or hydrophilic properties of the material may be determined during the plasma processing steps but can also be applied as a separate individual method. Hereinafter, these different possibilities will be described in more detail by means of plasma process sequences.

In FIG. 3 a plasma process sequence according to a preferred embodiment is illustrated. FIG. 4 shows a flow-chart of the method schematically illustrated in FIG. 3. The method according to this embodiment comprises "in-situ" monitoring of damage created during a plasma process performed to a low-k material. A first and a second step (step A and B in FIG. 3 and step 40 and 41 in FIG. 4), which may be optional, are used to clean a plasma chamber 20 comprising a wafer holder 21, also referred to as chuck, for holding the wafer 22 comprising the low-k material. The first step (step (A) in FIG. 3) is similar to prior art methods and may comprise a chamber cleaning step which uses for example an O$_2$/SF$_6$ or an O$_2$Cl$_2$ plasma. This step may also be referred to as Waferless Auto Cleaning (WAC). An additional, also optional, cleaning step (step (B) in FIG. 3), which is different from the prior art methods, may be introduced to remove residues, e.g. oxygen possibly present at chamber walls 23 and originating from previous processes. Steps (C) to (E) in FIG. 3 and corresponding steps 42 to 44 in FIG. 4 illustrate steps, similar to the steps for the prior art process described above. Step C illustrates the step of fixing the wafer 22 comprising the low-k material to the chuck 21, also referred to as chucking. The next step (step (D)) is a plasma process step which can for example be a reactive ion etching of the low-k dielectric material or a resist stripping step using e.g. an O-rich plasma 24. This step may cause damage to the low-k dielectric by replacing hydrophobic groups by hydrophilic groups. This allows moisture, e.g. water to adsorb in or to the pores of the low-k material, thereby increasing its dielectric constant. After finalizing the plasma process step, a gas stabilization step (step (E)) is introduced to remove reactant gasses (indicated by arrow 25). Steps C to E can, if desired, be repeated in order to perform more than one plasma process to the low-k material in the plasma chamber 20.

In a last step (step F in FIG. 3 and step 45 in FIG. 4), the wafer 22 may be released from the wafer holder 21, also referred to as electrostatic de-chuck, using e.g. a He plasma (e.g. 400 W, 12 eV, 6 seconds, gas pressure 20 mTorr). In this step, the wafer 22 is exposed to a noble gas plasma 26, e.g. a He plasma to discharge the wafer 22. According to this preferred embodiment, the de-chucking step may be combined with the step of monitoring the plasma damage, in accordance with preferred embodiments. According to embodiments of the present embodiment, the He plasma for de-chucking the wafer 22 also plays the role of noble gas plasma 26 to emit Extreme Ultra Violet and/or Vacuum Ultra Violet photons having sufficient energy to cause photolysis of water molecules adsorbed to the low-k material thereby releasing oxygen, hydrogen and/or hydroxyl radicals. EOS may be used to monitor the signal at a wavelength of 777 nm in order to quantify the amount of oxygen radicals released from the low-k material by the He plasma. The radiation emitted at a wavelength of 777 nm, or, in other words, the size of the radiation peak at 777 nm, is proportional to the detected amount of oxygen radicals and thus is a measure for the hydrophilic and/or hydrophobic properties of the low-k material. The hydrophilic and/or hydrophobic properties of the material then are a measure for the amount of damage caused to the low-k material by the plasma processes applied to it.

As an illustration, FIG. 5 shows an optical emission spectrum for a signal at wavelength of 777 nm which corresponds to a 5P→5S transition of electronically excited oxygen radicals. In case that, in addition to the degree of damage caused to the low-k material, also the depth of the damage into the material needs to be known, the total amount of adsorbed water needs to be removed or converted to oxygen radicals. This may be done by exposing the material to the He plasma for a sufficient time period, i.e. up to the moment when emission intensity reaches a background level. Then, an integrated signal during the time of exposure needs to be calculated which may then be a measure for the depth of damage (see further).

Figure 7:
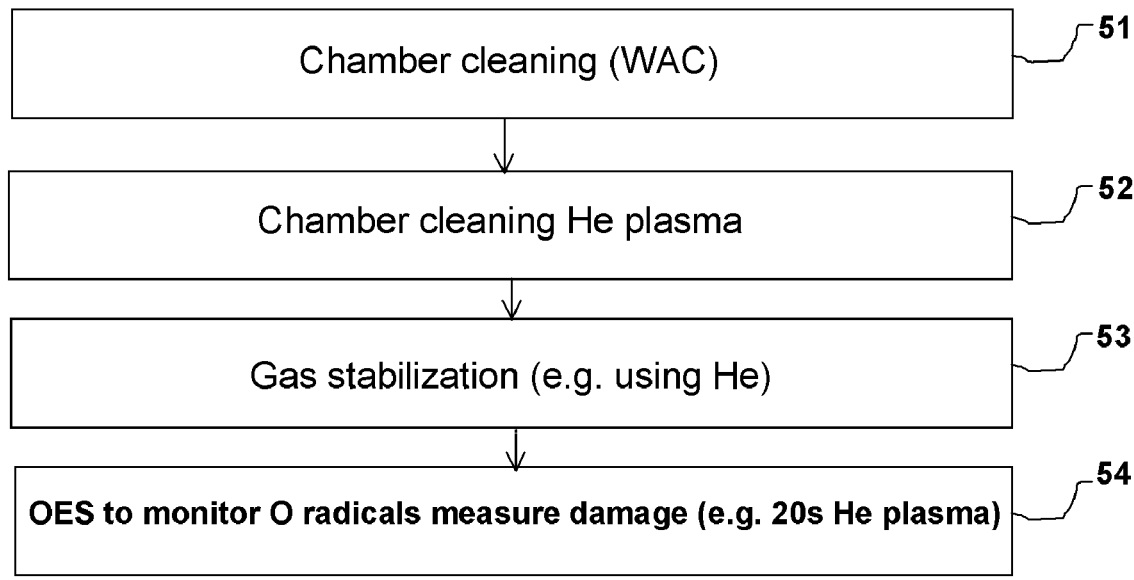
FIG. 7 shows a flow chart illustrating main processing steps of the method schematically illustrated in FIG. 6.

In FIGS. 6 and 7, another preferred embodiment of the method is illustrated. FIG. 6 schematically illustrates "ex-situ" monitoring of damage created during a plasma process performed to a low-k material. FIG. 7 shows a flow-chart of the method schematically illustrated in FIG. 6. According to this embodiment, a wafer 22 comprising the low-k material is first transferred to a first plasma chamber 20 where plasma processing, such as plasma etching and/or stripping is performed. This may be done similarly to the steps as described for the above embodiment with respect to FIG. 3, steps (A) to (F), except that now the de-chucking step and monitoring the damage caused to the low-k dielectric are not performed simultaneously. After de-chucking the wafer 22 from the wafer holder 21, the wafer 20 is transferred to a second plasma chamber 27 which is equipped with e.g. an OES tool to analyze damage caused to the low-k material. FIG. 6 illustrates the steps of cleaning the plasma chamber 27 (steps (A) and (B) in FIG. 6 and steps 51 and 52 in FIG. 7, similar to steps (A) and (B), respectively 40 and 41 with respect to FIGS. 3 and 4), introducing the noble gas plasma 26, e.g. He plasma (step (C) in FIG. 6 and step 53 in FIG. 7), and the plasma exposure step itself (step (D) in FIG. 6 and step 54 in FIG. 7). The noble gas plasma 26 may, for example be a He plasma with a power of 400 W, 12 eV, for a time period of 20 seconds and with a gas pressure 20 mTorr. EOS may be used to monitor e.g. the O* radicals released by the noble gas plasma 26. The last step, i.e. exposure to the noble gas plasma 26, e.g. He plasma may also used to release the wafer 22 from the wafer holder 21.

Figure 8:
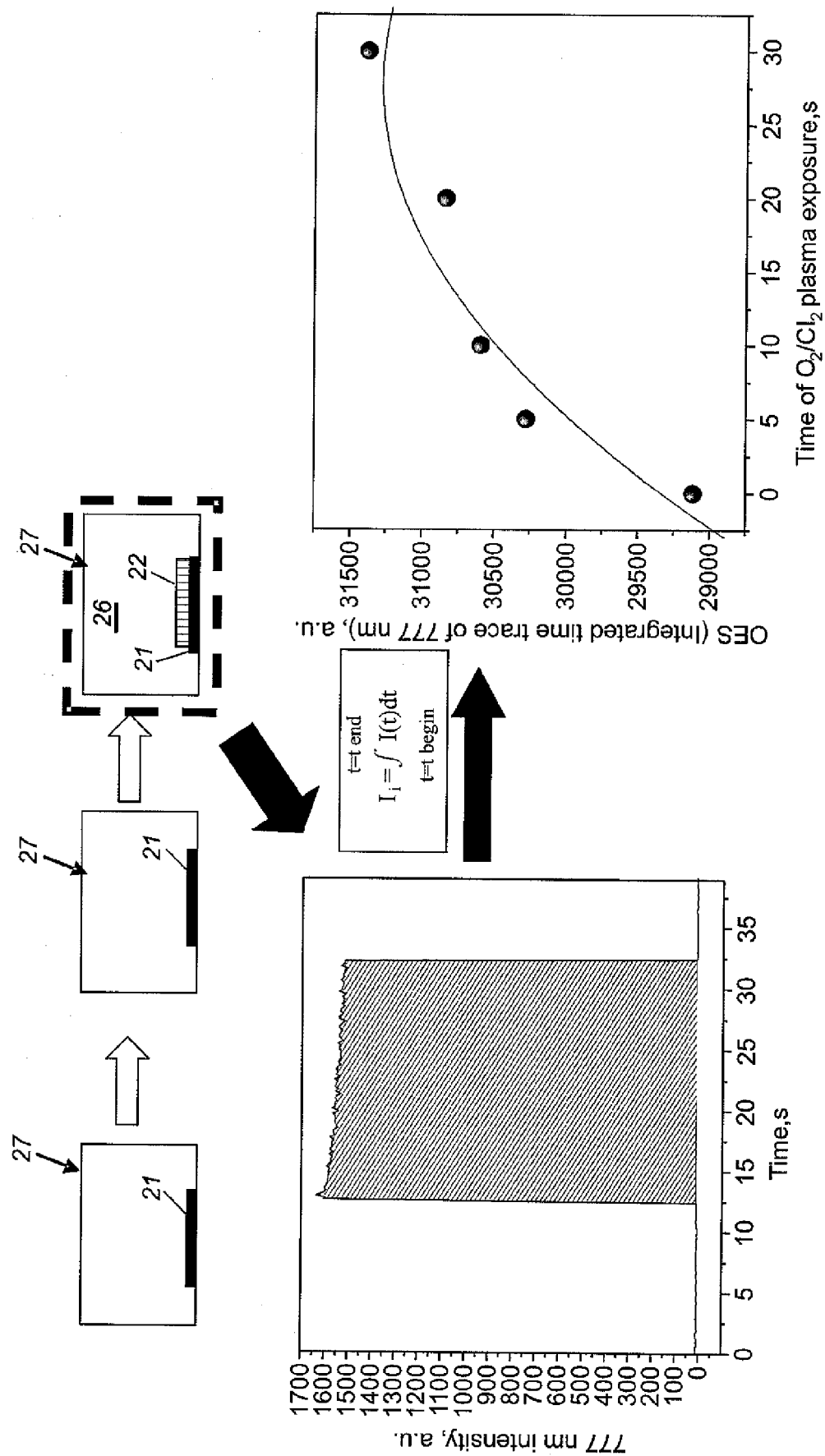
FIG. 8 illustrates different steps in a method according to preferred embodiments.

FIG. 8 gives a schematic overview of the method as discussed with respect to FIGS. 6 and 7. During exposure of the wafer 22 with the low-k material to the noble gas plasma 26, e.g. He plasma, EOS is used to monitor O* radicals released from water adsorbed to the low-k material by exposure to the noble gas plasma 26. The graph at the left of FIG. 8 shows the signal peak at 777 nm, i.e. the peak measured for O* radicals, observed in the EOS spectrum during exposure of the wafer 22 to the noble gas plasma 26, e.g. He plasma. The signal may then be integrated, which results in a graph as illustrated in the graph at the right of FIG. 8. This integrated signal gives a value for the degree of damage.

According to preferred embodiments, in addition to the degree of damage caused to the low-k material, also the depth of the damage into the material may need to be known. In that case, the total amount of adsorbed water needs to be removed or converted into, according to the example given, oxygen radicals. This may be done by exposing the material to the He plasma for a sufficient time period, e.g. up to the moment when emission intensity reaches a background level. Similar as described above, an EOS spectrum may be measured and the resulting signal may be integrated. The depth of damage may then be determined using this integrated signal.

Hereinafter, the method according to the preferred embodiments will further be illustrated by means of examples. It has to be understood that these examples are not intended to limit the invention. The method according to preferred embodiments may be applied to any material as described above.

EXAMPLE 1

Monitoring of Plasma Damage after $O_2/Cl_2$ Plasma Processing Using a He Plasma to Create Oxygen Radicals during De-Chucking Step (Ex-Situ)

Experiments were performed in an industrial plasma etch chamber 20 (LAM Versys 2300 STAR equipped with OES analyzer with spectral resolution of 2.5 nm). Wafer temperature during all the experiments was 30° C. Several plasmas were used in the whole processing sequence. An $O_2/SF_6$ plasma was used for waferless auto-cleaning (WAC) of plasma chamber sidewalls 23 and $O_2/Cl_2$ was used to simulate photoresist removal on the low-k material. A He plasma was used for removing the wafer 22 from the chuck 21 as well as for simultaneously releasing radicals from adsorbed water to the low-k material and thus to simultaneously monitor (or evaluate) plasma damage caused by the $O_2/Cl_2$ plasma to the low-k material.

The low-k material used in these experiments was porous carbon doped silica (BDIIx® obtainable from Applied Materials) deposited by Plasma Enhanced Chemical Vapor Deposition (PE-CVD). Porous low-k materials such as BDIIx® may typically be composed of silica and silsesquioxanes comprising organic hydrophobic groups. The exposure of these materials to an O-based plasma leads to the loss of the hydrophobic groups which are replaced by hydrophilic groups. As a result, hydrophilization of the material occurs during the plasma processes, e.g. stripping processes. The degree of hydrophilization corresponds to the degree of damage caused to the low-k material. The degree of damage caused to the low-k material may be proportional to the time of the $O_2/Cl_2$ plasma treatment.

In the present experiment, the porous low-k material was exposed to an $O_2/Cl_2$ plasma for different time periods. OES spectra were monitored at 777 nm "ex-situ" by exposing the material to a He plasma for 20 sec as described above. Next, the time trace of the 777 nm peak which was recorded during He plasma de-chucking was integrated (see higher with respect to FIG. 8). The integrated 777 nm intensity was plotted versus time of the $O_2/Cl_2$ plasma exposure (see FIG. 8, right hand graph). It was observed that the integrated O intensity increases with the duration of the $O_2/Cl_2$ exposure (e.g. stripping time). It can therefore be concluded that the 777 nm peak intensity during the de-chucking depends on the preceding treatment of the low-k material and thus depends on the amount of damage caused to the low-k material by this treatment. This gives information about the degree of damage which occurs in the plasma processing applied to the low-k material.

EXAMPLE 2

Correlation of FTIR and WEP with Chemiluminescence to Provide Quantitative Data about Degree of Plasma Damage Two alternative techniques were used to monitor plasma damage due to $O_2/Cl_2$ plasma exposure to a porous low-k material, i.e. Fourier Transform InfraRed (FTIR) and water based ellipsometric porosimetry (WEP).

Figure 9:
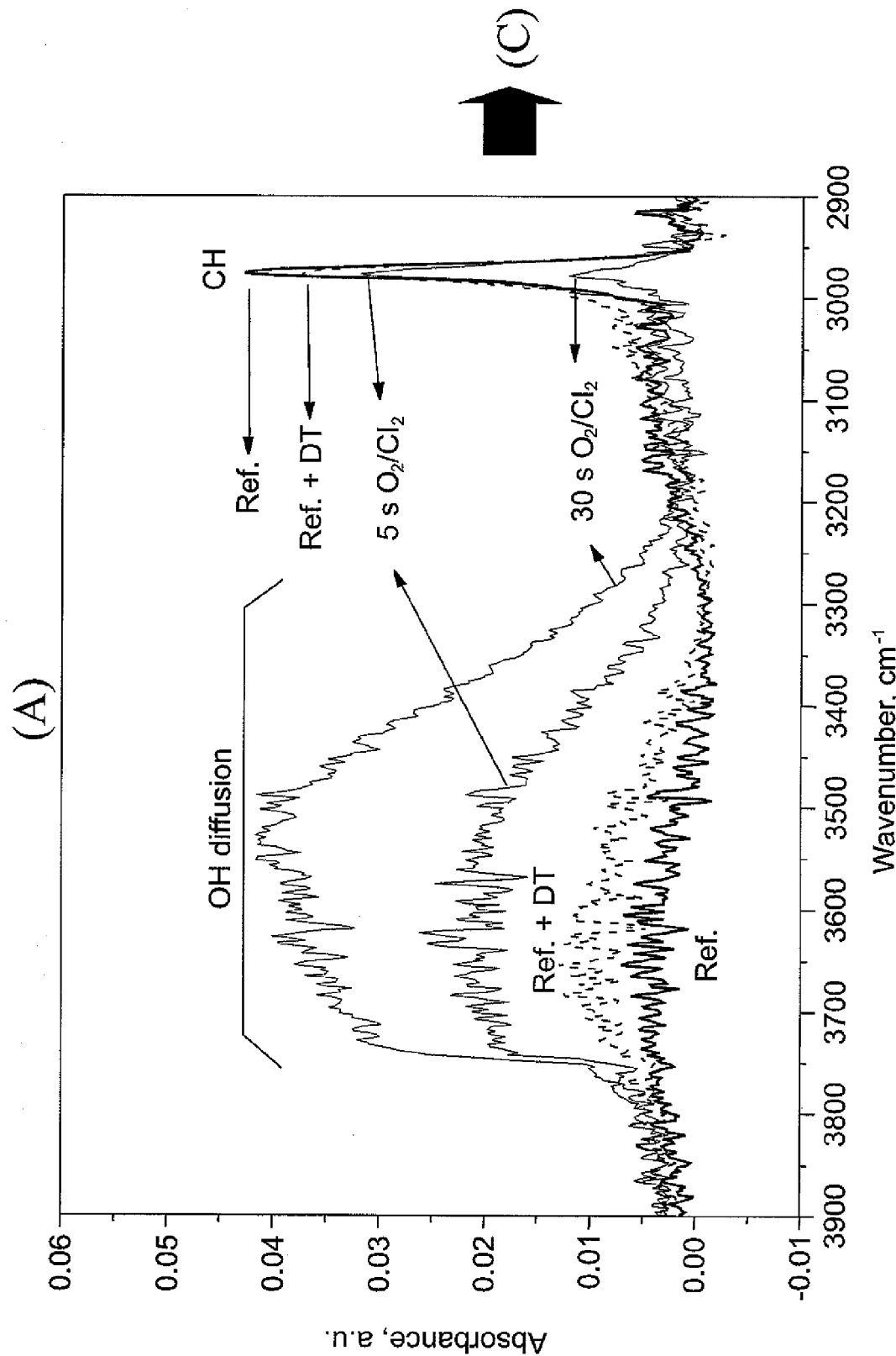
FIGS. 9 and 10 illustrate comparison and correlation of the method according to preferred embodiments with known analytical techniques to measure plasma damage in a material.
Figure 9:
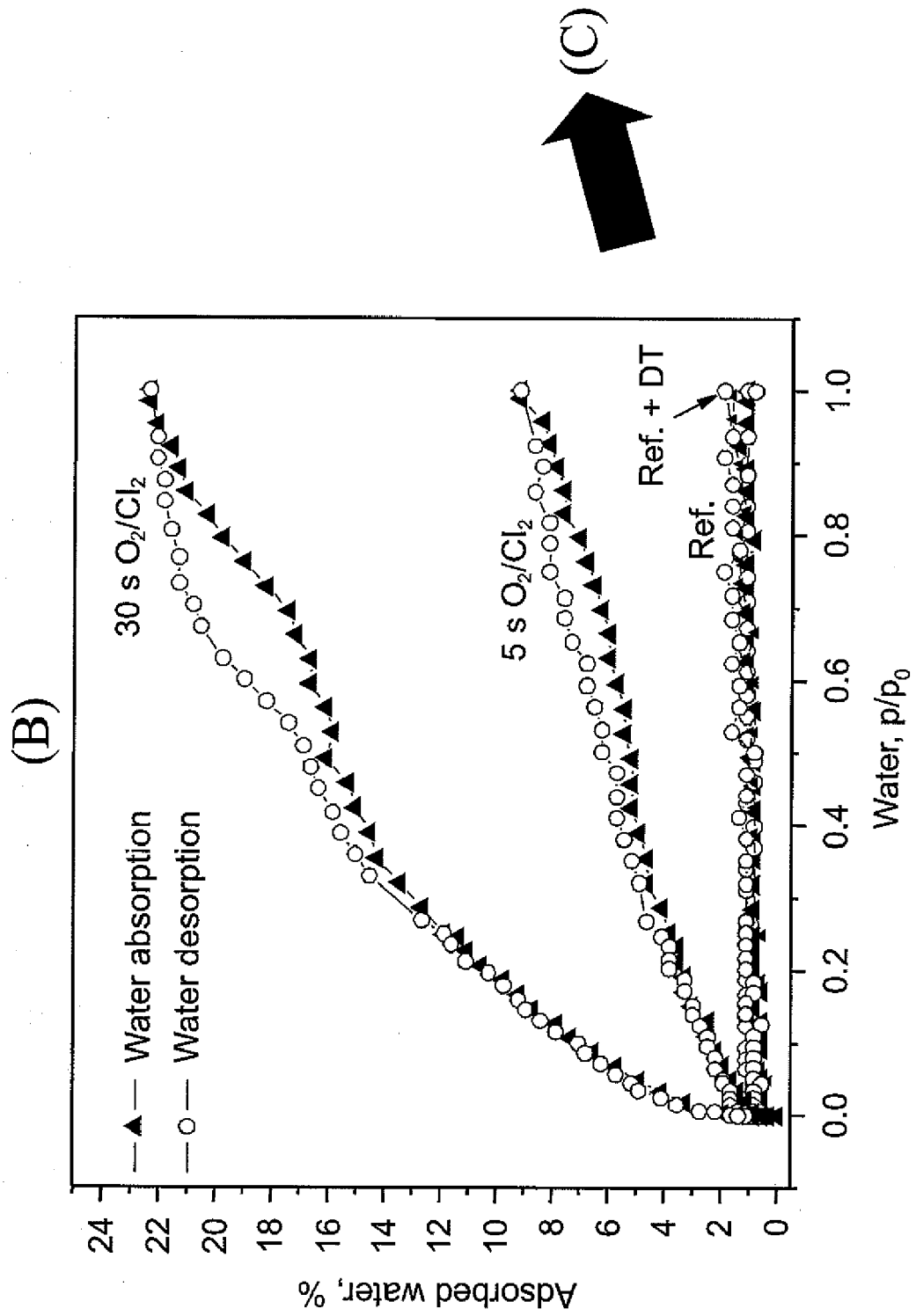
Figure 9:
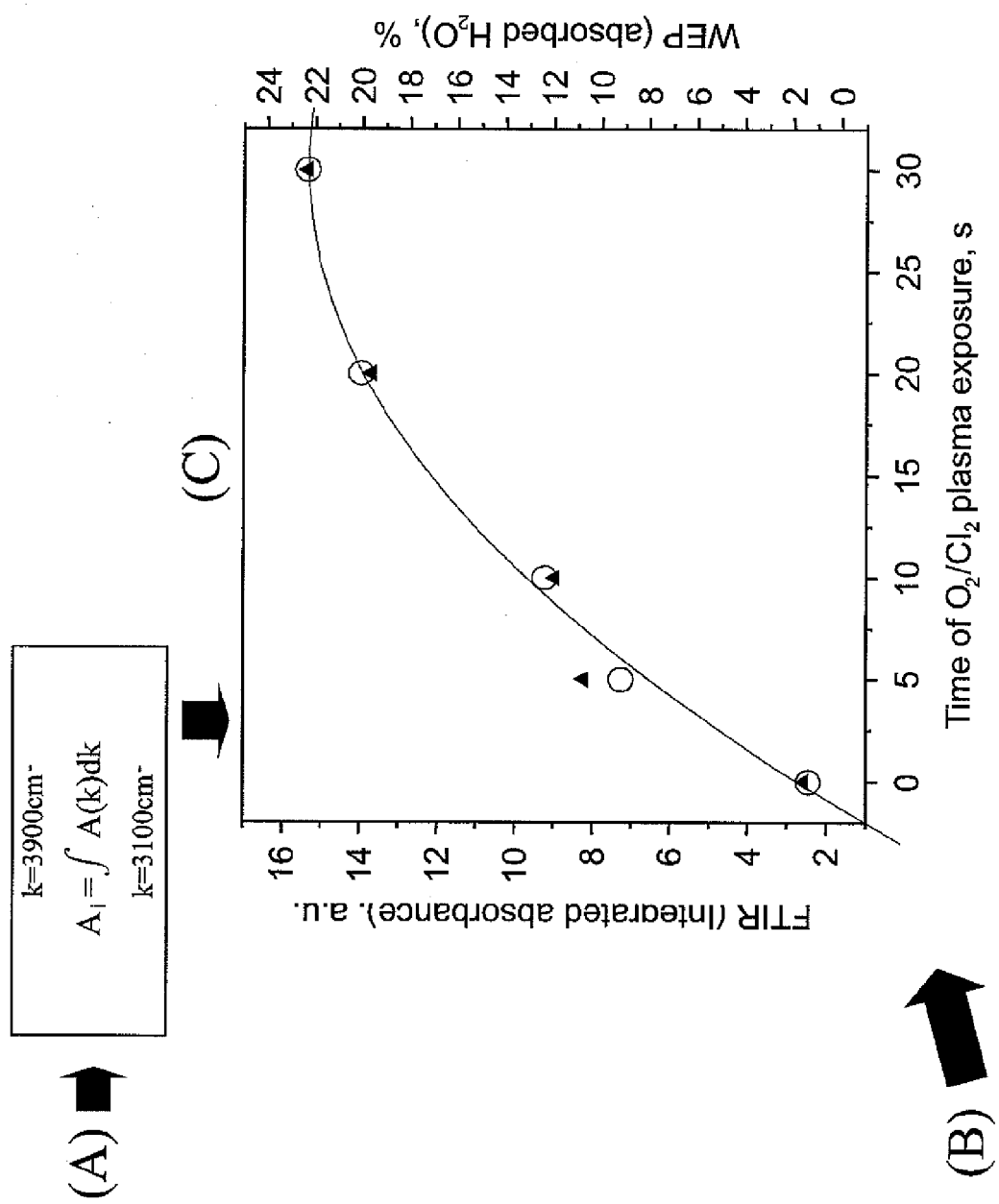

To monitor hydrophilic OH groups by FTIR the absorbance of silanol groups was monitored (see FIG. 9, (A)). Taking into account the fact that the degree of plasma damage is proportional to absorbance of —OH groups incorporated into the bulk of low-k materials, the degree of plasma damage can be evaluated. The absorbance of a pristine sample (non-damaged low-k material) was monitored first and the amplitude of OH groups is close to zero and intensity of the C—H peak is the highest one (corresponding to hydrophobic Si—$CH_3$ groups). This can be determined by FTIR, as mentioned before. Curve "Ref." in FIG. 9, (A) shows a reference sample exposed during 20 s to a He plasma that was used for the damage tests. The damaging effect of a He plasma is small in comparison with any O-based plasma chemistry. Curve "5 s $O_2/Cl_2$" in FIG. 6A represents a low-k sample damaged during 5 seconds by exposure to an $O_2/Cl_2$ plasma. As shown in this curve even a short exposure to an O-based plasma generates a significant amount of damage. The highest degree of damage is however observed after 30 seconds (s) of $O_2/Cl_2$ plasma exposure (curve "30 s $O_2/Cl_2$"). The amount of C—H groups was reduced almost five times in comparison to the pristine sample. The integrated absorbance of silanol groups is plotted versus time of $O_2/Cl_2$ plasma exposure in FIG. 9, (C). The FTIR signal is represented by triangles in the FIG. 9, (C).

Another method to estimate the degree of damage is WEP. This technique is based on ellipsometric measurements in a vacuum chamber which is filled with water vapour in a controllable way. Changes in the refractive index of a porous sample slowly filled with water can be recalculated into an amount of absorbed water in the sample pores. The amount of adsorbed water depends on hydrophobic properties of porous low-k materials. The amount of water absorbed into the pores of the low-k material at saturation pressure (the pressure at which 100% humidity exists in the chamber) was plotted versus $O_2/Cl_2$ exposure time (see FIG. 9, (B)). The water absorption number versus time of $O_2/Cl_2$ plasma exposure is compared to the FTIR result and plotted in FIG. 9, (C) (circles). In the case of the pristine sample (curve "Ref." in FIG. 9, (B)), the amount of absorbed water was around 1.6%. The sample treated by an exposure of 30 seconds to an $O_2/Cl_2$ plasma absorbed 22% of water at saturation pressure (see curve "30 s $O_2/Cl_2$" in FIG. 9, (B)). The amount of adsorbed water for the sample treated for 30 seconds was found to be equal to the total porosity of the low-k material. This means that the pore sidewalls were completely hydrophilic. Both FTIR and WEP are sensitive but complicated and time consuming methods to determine the hydrophobic properties of the low-k film and give similar results. Indeed, the degree of plasma damage is proportional to the time of $O_2/Cl_2$ plasma treatment.

Figure 10:
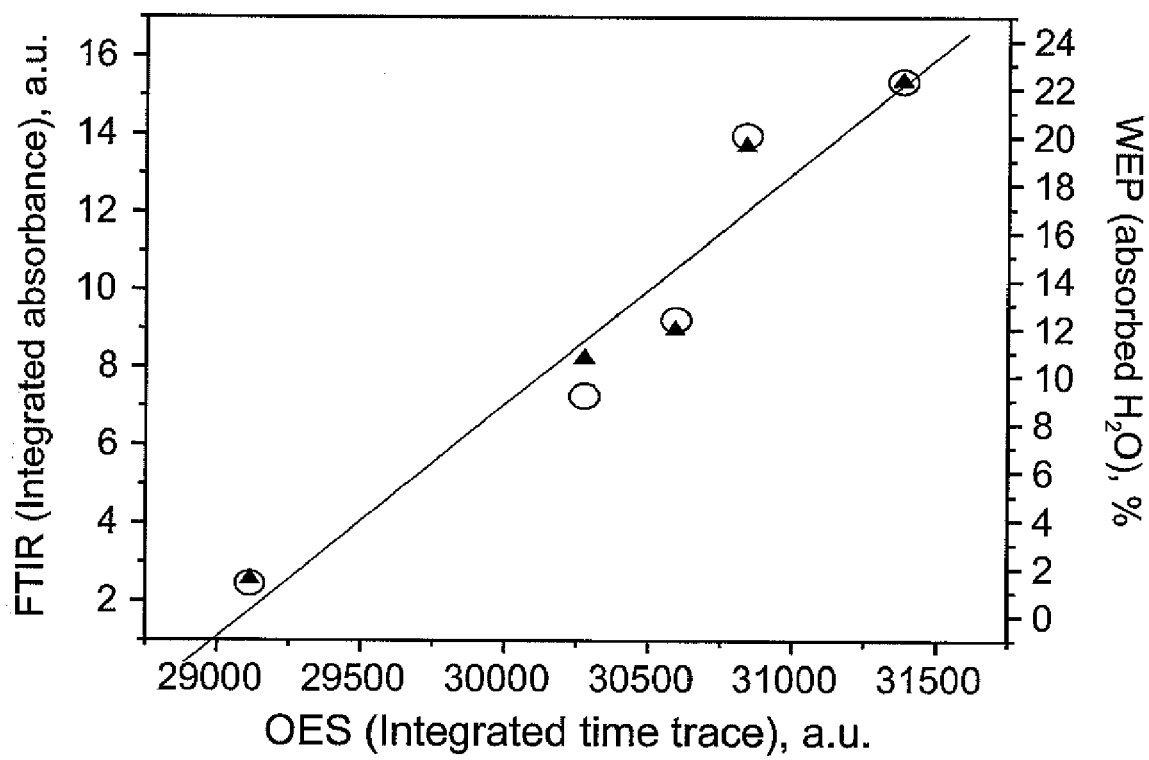

In order to compare OES, FTIR and WEP, the FTIR and WEP data as discussed In the previous paragraph are plotted versus the OES results as discussed in example 1 (identical samples and identical $O_2/Cl_2$ plasma exposures) in FIG. 10. It was found that the integrated time traces linearly correlate with both FTIR and WEP data. This proves that the integrated time traces of the 777 nm peak recorded during He plasma exposure of pristine and damaged low-k materials can be used as a method for evaluation of the degree of damage to low-k films. The integrated intensity of the emission of electronically excited O* radicals correlates with the degree of damage occurred during $O_2/Cl_2$ plasma strip.

The method according to preferred embodiments is faster and easier to perform compared to state of the art methods such as FTIR and EP because the method of the preferred embodiments does require almost no extra process steps and is non-destructive. In case the change in hydrophilic/hydrophobic properties due to plasma processing in a reactive ion etching chamber such as resist stripping needs to be quantified, the method may be performed in situ and no extra steps are required for monitoring the 777 nm signal as the evaluation step can be performed during the de-chucking step by using OES. Additionally the method according to preferred embodiments can be used to quantify plasma damage in e.g. patterned wafers which is rather impossible with existing techniques because they mostly are destructive.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for quantifying at least one of a hydrophilic property and a hydrophobic property of a material, the method comprising:
   exposing a material to a noble gas plasma, wherein the noble gas plasma emits at least one of Extreme Ultra Violet photons and Vacuum Ultra Violet photons having sufficient energy to cause photolysis of water molecules adsorbed by the material so as to release at least one of oxygen radicals, hydrogen radicals, and hydroxyl radicals;
   detecting an amount of at least one of released oxygen radicals, released hydrogen radicals, and released hydroxyl radicals; and
   quantifying at least one of a hydrophilic property and a hydrophobic property of the material based on the amount of at least one of the released oxygen radicals, the released hydrogen radicals, and the released hydroxyl radicals.

2. The method of claim 1, wherein detecting an amount of at least one of released oxygen radicals, released hydrogen radicals, and released hydroxyl radicals is performed by at least one method selected from the group consisting of optical emission spectroscopy, laser induced fluorescence, and mass spectrometry.

3. The method of claim 2, wherein detecting an amount of at least one of released oxygen radicals, released hydrogen radicals, and released hydroxyl radicals comprises detecting released oxygen radicals using optical emission spectroscopy at 777 nm.

4. The method of claim 1, wherein the method further comprises determining a degree of damage resulting from plasma processes performed on the material from the quantification of at least one of the hydrophilic property or hydrophobic property of the material.

5. The method of claim 1, wherein the method is performed in a reactive ion etching chamber using a He or Ar plasma.

6. The method of claim 1, wherein the method is performed "in-situ".

7. The method of claim 1, wherein the method is performed "ex-situ".

8. The method of claim 1, wherein the material is a porous material.

9. The method of claim 8, wherein the porous material is a low-k dielectric material having pores.

10. Use of the method of claim 1 for quantifying plasma damage of the material after etching of the material.

11. The method of claim 1, wherein the noble gas plasma consists essentially of noble gas plasma.

12. A method for quantifying plasma damage of a material after etching of that material, the method comprising:
   exposing a plasma etched material to a noble gas plasma, wherein the noble gas plasma emits at least one of Extreme Ultra Violet photons and Vacuum Ultra Violet photons having sufficient energy to cause photolysis of water molecules adsorbed by the material so as to release at least one of oxygen radicals, hydrogen radicals, and hydroxyl radicals;
   detecting an amount of at least one of released oxygen radicals, released hydrogen radicals, and released hydroxyl radicals;
   quantifying at least one of a hydrophilic property and a hydrophobic property of the material based on the amount of at least one of the released oxygen radicals, the released hydrogen radicals, and the released hydroxyl radicals; and
   using at least one of the quantified hydrophilic property and quantified hydrophobic property to quantify plasma damage to the material.

13. A method for detecting plasma damage in a low-k film, comprising:
   providing a wafer having a low-k film deposited thereon;
   subjecting the low-k film to plasma processing;
   dechucking the wafer by exposure to a He plasma, wherein the He plasma emits at least one of extreme ultra violet or vacuum ultra violet photons, and wherein the photons cause photolysis of water molecules generated as a reaction product during plasma damage and adsorbed onto the low-k film, thereby releasing at least one radical selected from the group consisting of oxygen radicals, hydrogen radicals and hydroxyl radicals; and
   measuring an intensity of radiation emitted at a wavelength characteristic of at least one of the radicals, wherein the intensity correlates with the at least one radical which correlates with an amount of water molecules present, wherein the amount of water molecules present correlates with a degree of plasma damage, wherein the wavelength for oxygen radicals is 777 nm, wherein the wavelength for hydrogen radicals is 656 nm, and wherein the wavelength for hydroxyl radicals is 309 nm.

14. The method of claim 13, wherein dechucking and measuring are conducted at a temperature of less than 150° C.

15. The method of claim 13, wherein dechucking and measuring are conducted at a temperature of less than 100° C.

16. The method of claim 13, wherein subjecting the low-k film to plasma processing is conducted at a temperature of from 20° C. to 200° C.

17. The method of claim 13, wherein the plasma processing is resist stripping.

18. The method of claim 13, wherein the water is adsorbed into pores of the low-k film.

19. The method of claim 13, comprising measuring an intensity of radiation emitted at a wavelength of 777 nm.

20. The method of claim 13, comprising measuring an intensity of radiation emitted at a wavelength of 656 nm.

21. The method of claim 13, comprising measuring an intensity of radiation emitted at a wavelength of 309 nm.

22. The method of claim 13, wherein the He plasma is generated under conditions of 400 W, 12 eV, 6 seconds, and a gas pressure of 20 mTorr.

23. The method of claim 13, wherein the He plasma is a low pressure plasma with a minimum power of approximately 100 Watt with no bias applied.

* * * * *

UNITED STATES PATENT AND TRADEMARK OFFICE
CERTIFICATE OF CORRECTION

PATENT NO. : 8,158,523 B2  Page 1 of 1
APPLICATION NO. : 12/204165
DATED : April 17, 2012
INVENTOR(S) : Urbanowicz et al.

It is certified that error appears in the above-identified patent and that said Letters Patent is hereby corrected as shown below:

| Issued Patent | | Description of Discrepancy |
|---|---|---|
| Column | Line | |
| Page 1 (Item 57) Abstract | 7 | Change "100-150 C." to --100-150° C.--. |
| Sheet 8 of 9 (x-axis) | 1 | Change "(Integrated" to --(Integrated--. |
| 1 | 63 | Change "O$_2$Cl$_2$" to --O$_2$/Cl$_2$--. |
| 4 | 59 | Change "figures" to --figure,--. |
| 5 | 25 | Change "onto from" to --onto/from--. |
| 8 | 49 | Change "O$_2$Cl$_2$" to --O$_2$/Cl$_2$--. |

Signed and Sealed this
Twenty-eighth Day of August, 2012

David J. Kappos
*Director of the United States Patent and Trademark Office*